US008185411B2

(12) United States Patent
Allard et al.

(10) Patent No.: US 8,185,411 B2
(45) Date of Patent: May 22, 2012

(54) METHOD, SYSTEM, AND APPARATUS FOR PATIENT CONTROLLED ACCESS OF MEDICAL RECORDS

(75) Inventors: David J. Allard, Boynton Beach, FL (US); Robert M. Szabo, Boca Raton, FL (US)

(73) Assignee: International Business Machines Corporation, Armonk, NY (US)

( * ) Notice: Subject to any disclaimer, the term of this patent is extended or adjusted under 35 U.S.C. 154(b) by 1849 days.

(21) Appl. No.: 10/780,098

(22) Filed: Feb. 17, 2004

(65) Prior Publication Data

US 2005/0182661 A1    Aug. 18, 2005

(51) Int. Cl.
*G06Q 10/00*    (2012.01)
*G06Q 50/00*    (2012.01)

(52) U.S. Cl. ................................. 705/3; 705/2
(58) Field of Classification Search .................... 705/2–3
See application file for complete search history.

(56) References Cited

U.S. PATENT DOCUMENTS

| | | | |
|---|---|---|---|
| 5,325,294 A | 6/1994 | Keene | |
| 6,023,765 A * | 2/2000 | Kuhn | 726/4 |
| 6,076,166 A * | 6/2000 | Moshfeghi et al. | 726/4 |
| 6,283,761 B1 * | 9/2001 | Joao | 434/236 |
| 6,347,329 B1 * | 2/2002 | Evans | 709/202 |
| 6,463,417 B1 | 10/2002 | Schoenberg | |
| 6,523,009 B1 | 2/2003 | Wilkins | |
| 6,988,075 B1 * | 1/2006 | Hacker | 705/3 |
| 2001/0041991 A1 | 11/2001 | Segal et al. | |
| 2001/0051881 A1 | 12/2001 | Filler | |
| 2002/0010679 A1 * | 1/2002 | Felsher | 705/51 |
| 2002/0026332 A1 * | 2/2002 | Snowden et al. | 705/3 |
| 2002/0120472 A1 | 8/2002 | Dvorak et al. | |
| 2002/0128870 A1 | 9/2002 | Whitson | |
| 2003/0055824 A1 | 3/2003 | Califano | |
| 2003/0074564 A1 | 4/2003 | Peterson | |
| 2003/0088439 A1 * | 5/2003 | Grushka | 705/2 |
| 2005/0159984 A1 * | 7/2005 | Hirano et al. | 705/3 |

OTHER PUBLICATIONS

Kenneth D Mandl, Peter Szolovits, Isaac S Kohane, David Markwell, and Rhona MacDonald. Public standards and patients' control: how to keep electronic medical records accessible but private • Commentary: Open approaches to electronic patient records • Commentary: A patient's viewpoint BMJ, Feb. 2001; 322: 283-287.*
Roy Schoenberg, Charles Safran. Internet based repository of medical records that retains patient confidentiality BMJ, Nov. 2000; 321: 1199-1203.*
"MedeFile—How It Works", MedeFile International, Inc., viewed Feb. 22, 2005.
Siggins, Corey, "A Lifeline, Online", Boca Raton News, Sep. 10, 2005.
White, Elizabeth, "Senate Wants Med Data High-Tech, Portable", Yahoo News, Associated Press, Nov. 18, 2005.

* cited by examiner

*Primary Examiner* — Sheetal R Rangrej
(74) *Attorney, Agent, or Firm* — Novak Druce + Quigg LLP

(57) ABSTRACT

A method of permitting controlled access to medical information can include establishing a storage means for containing medical information and establishing a means for accessing the medical information. The method further can include controlling the means for accessing the medical information according to a type of entity accessing the medical information, wherein access is limited according to the type of entity.

12 Claims, 1 Drawing Sheet

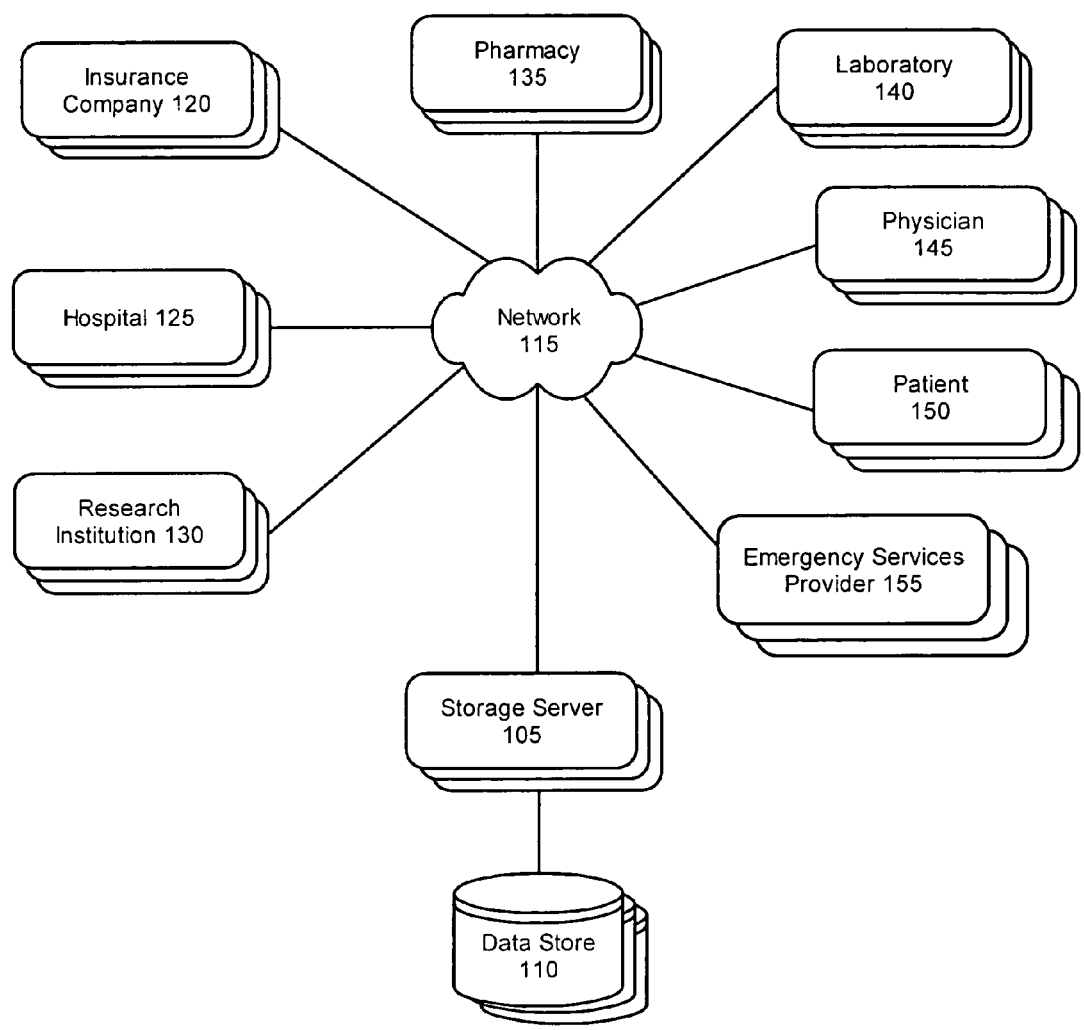

METHOD, SYSTEM, AND APPARATUS FOR PATIENT CONTROLLED ACCESS OF MEDICAL RECORDS

BACKGROUND

1. Field of the Invention

The present invention relates to the field of information administration and, more particularly, to user-specific information services.

2. Description of the Related Art

The storage and availability of different types of personal information is prompting increased privacy concerns. Users have a need to collect and store their personal information while also having ready access to the information. One of the manners in which information may be stored and retrieved more easily is through the use of electronic storage media. Users can store information such as bank records, medical records, credit card information, and the like on media. Unless the media is available to be accessed from different locations, however, the users must either carry the media with them or must permit access to the media from different locations. The latter situation results in concerns by the users that their personal information will not remain private and can be accessed without their permission.

This concern is especially true for medical records. Patient records need to be available for reference at their current doctors' offices, at any hospital where a patient is admitted or goes for outpatient treatment, and, for some limited purposes, at health insurance companies. At the current time, copies of private medical information are commonly scattered over different locations. In many of these instances, critical documents or images in hardcopies might even be lost, unavailable, or temporarily misplaced.

In all instances, doctors, hospitals, and health insurance employees all have to be trusted to have adequate computer and physical security over this medical information. Additionally, records may remain in the possession of particular doctors long after a patient has changed doctors and/or insurance companies, with no real need or incentive for those doctors or companies to provide access, maintain the confidentiality of this information, or ensure its security. The end result is that patients currently have no control over enabling and limiting access to their private medical information.

Currently, there is only limited physical security for many paper records at doctors' offices. For computer records, there are no guarantees, and limited regulatory requirements mandating that these records be kept secure from unauthorized personnel and/or hackers. Further, as many people have illnesses or conditions that they wish to remain private, this lack of security may result in exclusion from a job, affordable insurance, or embarrassing circumstances for these individuals should their private medical information become accessed by someone without the individual's permission.

Accordingly, it would be beneficial to provide a system and method that would permit a patient to access their own medical records. It would also be beneficial to provide a system and method that would permit a patient to control who could view their medical records as well as how such persons or entities would be able to view such information. It would also be beneficial to provide a system and method that would increase security over a patient's medical records consistent with local government regulations such as the Health Insurance Portability and Accountability Act in the United States.

SUMMARY OF THE INVENTION

The present invention provides a method, system, and apparatus for permitting a patient to have controlled access to their medical records. More specifically, the present invention is capable of permitting a patient to access their own medical records from any location such that they are available even if the patient is away from their home. The present invention would also be capable of increasing the level of security a patient had over their medical records and enabling a patient to control those persons with whom access was granted to view these records.

In general, the present invention provides a method of permitting controlled access to medical records wherein a repository or storage server is first established. The repository would include each patient's records and would store them using a data storage device. The repository may be a central repository or a plurality of regional repositories. The repository may be connected to a network through a secure mechanism. As a result, any of a number of different persons and/or institutions may be granted access to the repository by the patient including, but not limited to, insurance companies, hospitals, research institutions, pharmacies, laboratories, and physicians. Authorization to access the repository may be through the use of a card and/or PIN for each of these persons and/or institutions, and some access may be limited in scope to only those records necessary for that particular person and/or institution.

In one embodiment, the present invention provides a method for permitting controlled access to medical records involving the steps of establishing a storage means for containing medical information, establishing a means for accessing the medical information, and controlling the means for accessing the medical information. Access to the medical information can be controlled according to a type or assigned role of the entity accessing the medical information, wherein access is limited according to the type or role of the entity.

In another embodiment, the present invention provides a machine-readable storage having stored thereon, a computer program having a plurality of code sections, said code sections executable by a machine for causing the machine to perform the steps of establishing a storage means for containing medical information, establishing a means for accessing the medical information, and controlling the means for accessing the medical information. Access to the medical information can be controlled according to a type or an assigned role of the entity accessing the medical information, wherein access is limited according to the type or role of the entity.

In yet another embodiment, the present invention provides a system for permitting controlled access to medical records including storage means for containing medical information, means for accessing the medical information, and means for controlling the means for accessing the medical information. Access to the medical information can be controlled according to a type or assigned role of the entity accessing the medical information, wherein access is limited according to the type or role of the entity.

BRIEF DESCRIPTION OF THE DRAWINGS

There are shown in the drawings, embodiments which are presently preferred, it being understood, however, that the invention is not limited to the precise arrangements and instrumentalities shown.

FIG. 1 is a schematic diagram illustrating one embodiment of a system for permitting controlled access to medical records in accordance with the inventive arrangements disclosed herein.

DETAILED DESCRIPTION OF THE INVENTION

The present invention provides a method, system, and apparatus for permitting controlled access to personal information including, but not limited to, medical records. More specifically, the present invention provides a storage location for personal information that stores the information securely and only provides the information to authorized persons to whom the patient has given authority to view and/or use the information, or a subset of the information.

In one embodiment, patients can specify which person or entity may access one's medical information, which portions of the medical information such persons can access, as well as how such information can be viewed. These determinations can be based upon the role or type of entity accessing the information. For example, a research institution can be provided with different aspects of a person's medical information than a doctor. By differentiating access based upon the accessing party's role, anonymous information, for instance, can be provided to a researcher, while a patient's full medical information can be provided to a personal physician. As such, the present invention gives maximum control to the patient and/or eliminates static and potentially out-of-date copies of information from being spread around potentially hundreds of locations.

The present invention permits a patient to access their medical information from any location by establishing a central or distributed repository to which a patient may have their personal information sent and maintained. The main purpose of the repository would be to securely store the medical information and permit only authorized access to the information. The patient would have complete control over the information and those individuals who would be capable of accessing the information. In an emergency situation, however, the present invention contemplates that precertified emergency care providers would be able to override the access limitations to obtain necessary medical information in a manner that would remain highly secure.

In one embodiment, the present invention can utilize a central data repository or a series of repositories that are used to store medical information. A patient would supply their medical information to the repository and request providers to do the same. Each patient would have a universally unique patient identifier. The identifier may be any identifier, such as an alphanumeric sequence, that may then be used to tag each record of the patient's medical information. In another embodiment, the identifier may be recorded on a card with a magnetic strip or on a smart card having a radio frequency identification (RFID) tag with the number stored therein. Still, any of a variety of portable and/or personal storage devices may be used to record such information. In an alternative more secure embodiment, a smart card, such as the RSA SecurID 6100 USB Token, could be used to provide secure mobile patient credentials, or any active security measures, which may include biometrics, private keys, etc.

In any case, the card may be associated with a secret personal identification number (PIN) that is used to control access. The PIN may be a number or may include letters. The PIN may be randomly generated and assigned to the patient or may be specifically chosen by the patient. The PIN may be used to further increase the security over the patient's medical information by ensuring that an unauthorized person could not access medical information simply by using a card.

In alternative embodiments, a patient may obtain additional cards that may be given to family members. As such, in an emergency situation and/or when the patient is not able to access the information themselves, the family member may access the patient's information with the card and, in select embodiments, their own PIN. The PIN may be the patient's PIN or a different PIN. Each provider would be issued their own card and PIN, which permits the system to record which person accessed the patient's medical information, what information was accessed by that person, and limits access to specific content as directed by the patient.

Accordingly, when a patient desires to access their records, they may do so by providing their unique patient identifier, card, and/or PIN to the repository. At that time, the patient has secure access to their records regardless of the location of the patient at any given time.

If the patient wishes to grant access to others, this may be accomplished using a variety of different procedures that safeguard the patient and the patient's information. In one such example, such as when visiting a physician or hospital, the patient would be able to grant access to the physician or hospital by authorizing the physician or hospital to access the patient's records. The doctor's office or hospital would have a reader for reading the patient's card. The reader may be capable of reading magnetic strips, RFID tags, or smart cards, with or without active security features based on biometrics etc. In select embodiments, RFID tags are used with smart cards as RFID tags utilize encryption that is generally more difficult to compromise than magnetic strips. The reader would be specific to the type of media chosen for deployment.

Accordingly, once in the physician's office or hospital, the patient would use their card to identify themselves to the repository Web site. The link to the site may be secured by known means, including, but not limited to, a secured socket layer (SSL) connection, public/private key encryption, or through a virtual private network (VPN). The card and/or PIN would identify the patient to the repository. A cookie or other identifier on a workstation at the physician's office could be used to identify the physician's office and permit the patient to quickly navigate to the correct physician and grant that physician access.

In one embodiment, while the patient is connected, a list of current accessors would also be visible or available to be viewed. The patient could then remove one or more access permissions from their profile on the system thereby keeping the system up to date and/or increasing the security of the patient's information. For example, as access can be granted to parties based upon that parties assigned role, the patient can change the role of an accessor thereby discontinuing that party's privileges. For instance, the role of a physician can be changed from "current medical provider" where the physician has unfettered access to the patient's medical information, to "past medical provider", where the physician has limited or no access to the patient's medical information. Any such changes can alter the access granted to the accessing party including, but not limited to, which items of medical information are available to the accessor, how that information will be viewed, as well as whether the accessor will continue to have access to the patient's medical information at all.

Permitting a physician to have a card and/or PIN would allow the physician to access the patient's records at other times besides those instances when the patient is in the physician's office. For example, the physician would use a single card or mechanism to access medical information for each of that physician's patients. Each patient, being the administrator of his or her own information, would grant the physician access to his or her medical information. The physician, being registered with the present invention and having a PIN and providing that PIN to the system, would then be granted access to the medical information of each patient that granted the physician access.

In one embodiment, the present invention can be configured to require that a PIN be re-entered after a short time out period or period of inactivity, but would be long enough to permit a doctor to see patients in the same office without having to continually re-enter the PIN during the patient's visit. To expedite the process of accessing and retrieving a patient's records, a patient's card could be scanned upon entry to the physician's examination room. This would only provide an automated means to identify the patient and retrieve the records. After a patient has given a physician access, the physician may navigate to the patient's records at any time. These records would not be visible, however, until the physician enters the room and scans the physician's card (providing that a timeout has not occurred which would require the patient to re-enter the patient's PIN).

In an alternative embodiment, the action of the physician scanning the physician's card could also deactivate the view of any prior terminal that the physician was viewing in another room, thereby increasing the security of the prior patient's records. In another alternative embodiment, the physician's access could be through a wireless device over a secure fabric that would pull records from an active transient copy located on the physician's office server.

In some instances, the physician's staff may need to view a patient's records for some limited information. Such can be the case with respect to patient's test results. Still, this limited information may include, but is not limited to, verification that the patient is still covered by insurance, whether the patient's insurance provider has changed, whether the physician still has access to the patient's records, and/or whether the patient's insurance will cover a particular treatment and, if so, to what extent. As such, in another embodiment of the present invention, limited access may be granted by using a separate card and/or PIN that would provide limited access only from a specific office and only for patients that are associated with that office. A physician and/or the patient would be able to assign and/or delete this manner of limited access.

For example, a role of medical office worker can be created which allows a person with such a designation to access limited medical information that may be necessary for processing bills and claims. Patients can authorize a physician or physician's office. The physician, or office, in turn, can associate one or more office workers with this role such that when a patient authorizes a particular physician or office, that physician's office workers are provided limited access to the patient's medical information as defined by the role "medical office worker".

The system and method of the present invention may also be used to grant insurance companies with access to the patient's medical information to give these companies a paperless connection to the physician and patient files. In those embodiments where an insurance company is granted permission, the patient would be the person who would add or delete access to the patient's medical information. The access could be granted to one or more insurance companies and could be removed from those companies with whom the patient no longer has a relationship. Insurance company access could be limited as to the type of information that could be accessed. For example, only information essential for servicing claims, such as a procedure, a reference number, and provider information would be transferred to the insurance company. The reference numbers and procedures could then be correlated to a patient by the insurance company. A statement of this type of transfer could be associated with the reference number. Correlation to a particular patient's name could be set up as requiring additional authorization.

In alternative embodiments, prescriptions could be recorded into the repository and could be pre-authorized by the insurance company and processed by a pharmacist that is selected by the patient and recorded in the system. A patient's card could also be used for identification at the pharmacy for collection of the medicine.

In further embodiments, the present invention may include additional roles specifying the manner in which limited access may be granted. For example, a laboratory that is performing tests may be able to access the system as needed for information relevant to the tests performed. Using the lab's card and/or PIN would enable the patient to keep track of who had accessed the patient's information.

In yet another embodiment, a role can be created for research institutes. Patients can specify whether entities assigned such roles, or particular research entities for that matter, can access the patient's medical information. Accordingly, research institutes, using their own card and/or PIN, can access and/or search the repository to view medical information for those patients that chose to make medical information available to research institutes.

For example, such a system would allow a research institute to search for and obtain information regarding people with certain conditions. That information can be provided, however, in an anonymous fashion without information that identifies the patient and in a manner that is consistent with local government regulations and the patient's personal preferences. This would enable the research institute to find suitable subjects while maintaining anonymity and giving the patient ultimate control over whether his or her information was used by such entities. The patient may also be compensated for permitting some of their information to be available and used by the research institution. Again, although the patient can be compensated, for example through the present invention, the research institute need not be aware of the identity of the person having provided access to medical information.

In an alternative embodiment, the present invention may also include a failsafe provision in the event that a patient is physically or mentally unable to obtain medical information in an emergency situation. In this instance, the system and method may be designed to include emergency protocols such that a hospital or physician that has been registered as an emergency care provider, in an emergency situation, could access the system and obtain medical information about the patient by using a security override procedure. A patient may be given the option to opt out of the emergency override access, or designate only a subset of their medical information to be provided in these cases. In these instances, the system could be set up to record the identity and location of the person accessing the information using such an emergency override feature, the reason for the override, and the records that were accessed in order to prevent abuses.

In another embodiment of the present invention, the system and method may include an option whereby the patient is notified whenever their medical information is accessed. As such, the patient may keep track of who accesses the system, what was accessed, and when, thereby further ensuring the security of the patient's medical information. The patient may be notified by any suitable means including, but not limited to, fax, email, text messaging, automated or manual phone calls, and the like.

The present invention provides a system and apparatus for permitting controlled access to medical records. The present invention can also include a method of providing the service of controlling access to medical records for individuals. As noted, individuals would subscribe to the service and grant or revoke access to specific users or groups of users with specific rolls.

Thus, a patient can register with the system and log on from time to time to add entities to the patient's profile. Such entities can be registered with the system and have an assigned role. This role can be used by the system to determine the type of access rights afforded to that entity when added to a profile by a patient. Still, a patient may alter any such roles as may be required.

When an accessing party attempts to access the medical information of a particular patient, the PIN or identifier assigned to the accessing party can be compared with the patient's profile to determine what, if any, access rights have been afforded to that party. The patient's medical information can be provided to the accessing party as determined by the role specified in the patient's profile.

FIG. 1 is a schematic diagram illustrating one embodiment of a system 100 of permitting controlled access to medical records according to one embodiment of the present invention. In the system 100, a repository or storage server 105 may be established. The repository 105 would include each patient's records and would store them within a data store 110, such as a data tape storage, hard disk, or the like. The repository 105 would be connected to a network 115 through a secure means, such as an SSL connection, using encryption, or through a VPN. At that point, any of a number of different persons and/or institutions may be granted access to the repository 105 by the patient 150. These persons and/or institutions may include, but are not limited to, an insurance company 120, a hospital 125, a research institution 130, a pharmacy 135, a laboratory 140, a physician 145, as well as the patient 150 from wherever the patient 150 is located.

As discussed, the authorization to access the repository 105 may be through the use of a card and/or PIN for each of these persons and/or institutions, and some access may be limited in scope to only those records necessary for that particular person and/or institution. As noted, access rights can be specified by one or more roles assigned to each accessor, which may or may not be customized by the owner of the medical information. In addition, in the event of an emergency, an emergency service provider 155, such as a physician, hospital or emergency medical technician, may be able to override the system to obtain necessary medical information.

The present invention may be realized in hardware, software, or a combination of hardware and software. The present invention may be realized in a centralized fashion in one computer system, or in a distributed fashion where different elements are spread across several interconnected computer systems. Any kind of computer system or other apparatus adapted for carrying out the methods described herein is suited. A typical combination of hardware and software may be a general purpose computer system with a computer program that, when being loaded and executed, controls the computer system such that it carries out the methods described herein.

The present invention also may be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention may be embodied in other forms without departing from the spirit or essential attributes thereof. Accordingly, reference should be made to the following claims, rather than to the foregoing specification, as indicating the scope of the invention.

What is claimed is:

1. A computer-implemented method of permitting controlled access to medical information of a patient, the method comprising:
supplying medical information of the patient to a central repository by the patient and any medical providers who have treated the patient;
storing and maintaining the medical information of the patient in the central repository;
accessing the medical information by the patient from an access device using a unique patient identifier and a patient PIN;
controlling by the patient an authorization and a scope of access to the medical information by modifying an access control list within the patient's profile when the patient is connected to the central repository, wherein the access control list lists each authorized user and the assigned role of each authorized user, wherein the scope of access includes which items of medical information are available to an assigned role and how that information will be viewed;
assigning each authorized user with a unique authorized user ID and an authorized user PIN; and
tracking and notifying the patient of an identity of a user who accessed the medical information, information that was accessed by the user, and when the user accessed the information.

2. The method of claim 1, wherein the access device is controlled using a universally unique identifier.

3. The method of claim 1, wherein said controlling step is overridden by a registered emergency provider.

4. The method of claim 1, wherein the patient is compensated for permitting some of the medical information to be available and used by a research institution.

5. The method of claim 1, wherein during a doctor visit the patient provides access to the medical information for a time period long enough to support the visit at which point the access times out.

6. The method of claim 1, wherein access to the patient's medical information expires when a physician logs into another room/appointment.

7. A machine-readable storage having stored thereon, a computer program having a plurality of code sections, said code sections executable by a machine for causing the machine to perform the steps of:
supplying medical information of the patient to a central repository by the patient and any medical providers who have treated the patient;
storing and maintaining the medical information of the patient in the central repository;
accessing the medical information by the patient from an access device using a unique patient identifier and a patient PIN;
controlling by the patient an authorization and a scope of access to the medical information by modifying an access control list within the patient's profile when the patient is connected to the central repository, wherein the access control list lists each authorized user and the assigned role of each authorized user, wherein the scope of access includes which items of medical information are available to an assigned role and how that information will be viewed;
assigning each authorized user with a unique authorized user ID and an authorized user PIN; and tracking and notifying the patient of an identity of a user who accessed the medical information, information that was accessed by the user, and when the user accessed the information.

8. The machine-readable storage of claim 7, wherein the access device is controlled using a universally unique identifier.

9. The machine-readable storage of claim 7, wherein said controlling step is overridden by a registered emergency provider.

10. A computer-implemented system for permitting controlled access to medical information of a patient, the system comprising:

a central repository for storing and maintaining medical information of the patient, the medical information of the patient being supplied to the central repository by the patient and any medical providers who have treated the patient;

an access device for accessing the medical information by the patient or any other authorized user, the patient accessing the medical information from the access device using a unique patient identifier and a patient PIN, each authorized user accessing the medical information from the access device using a unique authorized user ID and an authorized user PIN; and at least a processor configured to control by the patient an authorization and a scope of access to the medical information by modifying an access control list within the patient's profile when the patient is connected to the central repository, wherein the access control list lists each authorized user and the assigned role of each authorized user, wherein the scope of access includes which items of medical information are available to an assigned role and how that information will be viewed;

assign each authorized user with a unique authorized means for user ID and an authorized user PIN, and track and notify the patient of an identity of a user who accessed the medical information, information that was accessed by the user, and when the user accessed the information.

11. The system of claim 10, wherein the access device is controlled using a universally unique identifier.

12. The system of claim 10, wherein the access control is overridden by registered emergency providers.

* * * * *